United States Patent [19]

Rovati et al.

[11] Patent Number: 4,978,683
[45] Date of Patent: Dec. 18, 1990

[54] PROGLUMIDE AND PHARMACEUTICAL COMPOSITIONS CONTAINING IT FOR USE IN THE TREATMENT OF NEOPLASTIC AFFECTIONS

[75] Inventors: Angelo L. Rovati; Claudio L. Rovati, both of San Fruttuoso di Monza; Francesco Makovec, Monza, all of Italy

[73] Assignee: Rotta Research Laboratorium S.p.A., Milan, Italy

[21] Appl. No.: 900,152

[22] PCT Filed: Dec. 5, 1985

[86] PCT No.: PCT/EP85/00673
§ 371 Date: Aug. 13, 1986
§ 102(e) Date: Aug. 13, 1986

[87] PCT Pub. No.: WO86/03968
PCT Pub. Date: Jul. 17, 1986

[30] Foreign Application Priority Data

Dec. 27, 1984 [IT] Italy ............................... 68281 A/84

[51] Int. Cl.$^5$ .......................................... A61K 31/165
[52] U.S. Cl. .................................................. 514/617
[58] Field of Search ........................................ 514/617

[56] References Cited

PUBLICATIONS

The Merck Index, Tenth Edition, Merck & Co., 1983, Rahway, New York, (U.S.), See p. 1120, Monograph 7680 "Proglumide".

Surgical Forum, vol. 33, 1982, Owen E. Winsett et al. "Gastrin Stimulates Growth of Colon Cancer", pp. 384–386.

Gastroenterology, vol. 80, No. 5, 1981, B. Rae-Venter et al.: "Gastrin Receptors in Human Colon Carcinoma", p. 1256.

Surgical Forum, vol. 35, 1984, Proceedings for the 40th Annual Sessions of the Forum on Fundamental Surgical Problems 70th Clinical Congress, American College of Surgeons, San Francisco, Oct. 1984, P. Singh et al.: "Gastrin Receptors in a Mouse Colon Cancer Cell Line Responsive to Trophic Effects of Gastrin", pp. 205–206.

Digestive Dieases and Sciences, vol. 29, No. 8, Aug. Supplement 1984, P. Singh et al.: "Mouse Colon Cancer and Trophic Effects of Pentagastrin in Relation to Gastrin Receptor Levels in Vivo", p. 80S.

Surgical Forum, vol. 32, 1981, Courtney M. Townsend et al.: "Stimulation of Pancreatic Cancer Growth by Caerulein and Secretin", pp. 228–229.

Proc. Natl. Acad. Sci. U.S.A, vol. 78, No. 10, Oct. 1981, W. F. Hahne et al.: "Proglumide and Benzotript: Members of a Different Class of Cholecystokinin Receptor Antagonists", pp. 6304–6308.

Ann. Surg., vol. 202, No. 3, Sep. 1985, R. Daniel Beauchamp et al.: "Proglumide, a Gastrin Receptor Anatagonist, Inhibits Growth of Colon Cancer and Enhances Survival in Mice", pp. 303–309.

J. Clin Gastroenterol, vol. 5, No. 1, Feb. 1983, C. B. H. W. Lamers et al.: "The Effect of a Gastrin-Receptor Antagonist on Gastric Acid Secretion and Serum Gastrin in the Zollinger-Ellison Syndrome", pp. 21–25.

Rev. Med. Limoges, vol. 5, No. 3, 1974, R. Claude et al.: "Interet du Milide (*) dans le Traitement des Affections Gastroduodenales (a Propos de 30 cas)", pp. 183–187.

*Primary Examiner*—Jerome D. Goldberg
*Attorney, Agent, or Firm*—Sughrue, Mion, Zinn, Macpeak & Seas

[57] ABSTRACT

This inventions relates to a method of treating malignant tumors of the pancreatic, colic or gastric origin whose growth is increase by bioactive polypeptides comprising administering an anti-tumor effective amount of proglumide or pharmaceutical acceptables salt thereof to a patient afflicted with said malignant tumors.

2 Claims, No Drawings

PROGLUMIDE AND PHARMACEUTICAL COMPOSITIONS CONTAINING IT FOR USE IN THE TREATMENT OF NEOPLASTIC AFFECTIONS

The subject of the present invention is a new therapeutic use of D,L-4-benzamido-N,N-dipropyl-glutamic acid (proglumide) and its pharmaceutically-acceptable salts, for use in the treatment of neoplastic affections in which there is a pathological cell increase indirectly affected by gastrin, cholecystokinin (CCK), other bioactive peptides or by related mechanisms which are not yet well clarified.

The applicants have found that the said drug, already widely used in the treatment of gastric ulcers (see for example Merck Index No. 7680, 10th edition), in fact has an unexpected but extremely interesting therapeutic activity, which is that of significantly inhibiting the cell increase of tumour cells resulting from chemically induced pancreatic, colic or gastric cancer or of destroying such cells.

The invention is based on the discovery that the polypeptide hormone gastrin has a trophic effect on the digestive epithelium, just as the hormone CCK has a trophic action on pancreatic acini. Thus the chronic administration of gastrin to rats (or of pentagastrin which is the biologically active part of the physiological hormone) causes hyperplasia of the fundic and colic mucous membranes. Recently (Winsett et al—Surgical Forum, 33, 384 (1982)) it has been shown that gastrin stimulates the growth, in mice, of transplantable colic tumours obtained by chemical induction.

It has also been shown that the chronic treatment of rats with cerulein (a synthetic analog of CCK) causes hyperplasia of the pancreatic acinus cells (Solomon et. al.—An. J. Physiol 235, E714–719 (1978)).

On the basis of these theoretical premises, there has been a desire to experiment to see whether proglumide might behave as an antagonist to the growth of induced gastro-intestinal tumours and to evaluate whether this action could also affect the survival time of the animals.

This antitumoral activity of proglumide, which is the subject of the present invention, will thus be illustrated by a series of pharmacological experiments in vitro and in vivo arranged to show both the qualitative and quantitative aspects of the antitumoral activity and the mechanism by which this activity is manifested.

Experiment 1

Action of Proglumide on the rate of pentagastrin-induced growth of normal and tumoral colic cells Male mice having a weight of 20–25 g were innoculated subcutaneously in the interscapular region with a suspension of $8 \times 10^4$ colic-adenocarcinoma tumour cells taken from a mouse.

Four groups of 12 animals were used, that is: a group of control animals, a group of animals treated with 200 mg/kg i.p. doses of proglumide 3 times a day, a group of animals treated with 200 $\mu$g/kg of pentagastrin every eight hours and a group of animals treated with proglumide and pentagastrin in the manner indicated above.

After 20 days the animals were killed and the fundic mucous membranes and tumours were removed, weighed and extracted to determine the DNA. The results obtained are given in Table 1.

TABLE 1

Antagonistic activity of Proglumide towards the growth of colic tumours induced by pentagastrin

| GROUPS | No Animals | Dose | Weight of the mucous membrane (mg) | student's t | fundic DNA (mg) | student's t | weight of the colic tumour (mg) | student's t | tumour DNA (mg) | student's t |
|---|---|---|---|---|---|---|---|---|---|---|
| A: Control | 12 | — | 15.9 ± 1.44 | — | 0.21 ± 0.02 | — | 500 + 12.6 | — | 2.90 + 0.23 | — |
| B: Pentagastrin (PEG) | 10(ˆ) | 200 mcg/kg-3 per day | 40.9 ± 1.26 | 12.78(*) | 0.49 ± 0.03 | 9.46(*) | 800 ± 12.8 | 16.6(*) | 4.56 ± 0.46 | 3.37() |
| C: Proglumide (PR) | 12 | 200 mcg/kg-3 per day | 13.3 ± 1.58 | 1.21 | 0.12 ± 0.02 | 3.17(**) | 470 ± 11.5 | 1.75 | 2.54 ± 0.23 | 1.10 |
| D: PEG + PR | 12 | 200 mcg/KG PEG + 200 mg/kg PR | 16.0 ± 1.27 | vsA: 0.05 vsB: 13.7(*) | 0.21 ± 0.05 | vsA:0 vsB: 4.43(*) | 519 ± 11.8 | vsA: 1.11 vsB: 16.1(*) | 2.80 ± 0.24 | vsA: 0.32 vsB: 3.57() |

(ˆ)2 animals died during the treatment
(**)$p < 0.01$
(***)$p < 0.001$

The data given in the table show that PEG causes both significant hyperplasia of the fundic mucous membrane and a significant increase in the weight of the mucous membrane tumour and of the DNA content. However proglumide, at the doses used, is capable of inhibiting significantly both of the trophic actions of pentagastrin.

Experiment 2

Antagonism of proglumide to the rate of incorporation of tritiated thymidine in colic tumour cells, stimulated and unstimulated by pentagastrin The groups of animals and the treatments were identical to those given in the preceding experiment. On the seventh day, two hours after the final treatment, the animals were killed and the tumours which had developed were explanted.

Small pieces of tissue were incubated at 37° for 30 minutes in a Dulbecco-modified Eagle-type culture medium together with 2 $\mu$Ci of (3-H)-thymidine. The reaction was interrupted by the addition of 0.4N perchloric acid containing carrier thymidine. The samples were homogenised with 2 ml of 0.2N perchloric acid and RNA and proteins were removed by conventional techniques.

The DNA content of the samples was determined by the colorimetric method with diphenylamine (Biochem. J. 62, 315–323 (1956)).

The incorporation of the (3-H) thymidine in the DNA was determined by counting coupled aliquots of filtrate in a liquid scintillator under conditions suitable for counting the tritium.

The results were expressed as disintegrations per minute per microgram of DNA.

The results obtained are given in Table No. 2 and are expressed as a percentage variation with respect to the controls of the dpm of tritiated thymidine per mcg of DNA.

TABLE 2

Influence of Proglumide and Pentagastrine on the incorporation of tritiated thymidine in the synthesis of DNA in cultures of tumour cells in vitro.

| GROUPS | DOSE | % VARIATION WITH RESPECT TO THE CONTROL GROUP (mean ± S.E.) | STUDENT'S t (P) |
|---|---|---|---|
| A: Controls | | 100.0 ± 4.9 | |
| B: Pentagastrin (PEG) | 200 mcg/kg (3 per day) | 285.0 ± 20.3 | vsA:8.859 (<0.001) |
| C: Proglumide (PR) | 200 mg/kg (3 per day) | 88.2 ± 5.2 | vsA:1.65 |
| D: (PEG) + (PR) | 200 mcg PEG (3 per day) +200 mg PR (3 per day) | 112.0 ± 8.4 | vsA:1.24 vsB:7.88 (<0.001) |

From the data given in the table it is seen that pentagastrin accelerates the replication of DNA in colic tumour cells; in fact, at the doses used, the incorporation of tritiated thymidine, is found to be increased by about three times compared to the controls, an increase which, on a statistical basis, is highly significant.

Proglumide alone reduces the incorporation but not significantly, while the combined treatment with pentagastrin and proglumide means that the antagonistic action of the latter prevents the pentagastrin from reaching the target tissue and there is thus a clear reduction (statistically significant) in the incorporation of tritiated thymidine in the DNA compared with the group of animals treated solely with pentagastrin.

Experiment 3

In order to check the possibility that proglumide can influence the survival time of animals having a transplanted colic adenocarcinoma, the following experiment was carried out.

Male mice having a weight of 20–25 g were innoculated subcutaneously, in the interscapular region, with a suspension of $1 \times 10^5$ colic-adenocarcinoma tumour cells taken from a mouse. Four groups of 12 animals were used, that is: a group of control animals and three groups of animals treated with 100, 200 and 400 mg/kg i.p. doses of proglumide respectively, three times a day.

This treatment was continued up to the 35th day, the day on which the final control animal died. The straight line of regression for the survival time of the various groups, starting from the first day on which a death occurred was calculated by the least squares method. It was thus possible to calculate an ED50, that is, the single daily dose of the drug capable of increasing the survival time of the animals by 50%.

The results obtained are given in Table No. 3.

TABLE 3

Effect of Proglumide on the survival time of mice innoculated with colic adenocarcinoma.

| TREATMENT | DAYS ON WHICH DEATHS (INDICATED IN PARENTHESES OCCURRED) starting from time 0. | (%) DEATH TOTAL | CALCULATED STRAIGHT LINE OF REGRSSION (1) AND COEFFICIENT OF CORRELATION (r) | DAYS OF LIFE PER ANIMAL (AVERAGE) | ED60 |
|---|---|---|---|---|---|
| Control group | 17(1)-20(1)-22(2)-24(1)-26(2)-29(1)-30(1)-32(2)-35(1) | 100 | n° animals = 22.35 − 0.647 (r = 0.995) | 25.3 | — |
| Proglumide 100 mg/kp i.p. | 20(1)-24(1)-27(2)-29(1)-30(1)-33(1)-34(2) | 75 | n° animals = 22.47 − 0.545 (r = 0.98) | 30.1 | 342.9 (r = 0.99) |
| Proglumide 200 mg/kg i.p. | 22(1)-23(1)-25(1)-28(1)-30(2)-33(1)-35(1) | 66.6 | n° animals = 23.06 − 0.55 (r = 0.99) | 31.5 | |
| Proglumide 400 mg/kg i.p. | 23(1)-28(1)-31(1)-33(1) | 33.3 | n° animals = 18.82 − 32 (r = 0.98) | 40.4 | |

(1) The straight lines of regression were calculated from the day at which the first death occurred.

From an examination of the table it is seen that the treatment with proglumide significantly increases, and in a dose dependent manner, the survival time of animals innoculated with colic adenocarcinoma. This effect is probably related to the antagonistic action of proglumide towards endogenous gastrin which, as previously explained, has a stimulating effect on the growth of gastrointestinal tumour cells. An ED50 value of about 340 mg/kg was also calculated, this being the dose which enables the survival time of the animals to be doubled.

Experiment 4

Inhibiting action of proglumide on the rate of growth of pancreatic adenocarcinoma induced by CCK-8

Male hamsters were innoculated in the cheek pouch with a suspension of $1 \times 10^5$ pancreatic adenocarcinoma tumour cells. After five days from the innoculation the animals were divided at random into four groups of 10 animals each, that is a control group, a group of animals treated with 250 mg/kg i.p. of proglumide three times a day, and a fourth group treated with proglumide and CCK-8 in the manner described above.

After 15 days of this treatment the animals were killed and the normal pancreas and the pancreatic tumours introduced into the cheek pouches were removed and weighed. The DNA was extracted and measured by conventional techniques.

The results obtained are given in Table 4 where they are expressed as average values ± S.E.

The data given in the Table show that the hormone cholecystokinin (of which CCK-8 is the biologically active component), which has a trophic action on normal pancreatic cells, also stimulates the growth of pancreatic adenocarcinoma. Proglumide, which is a specific antagonist to CCK, antagonises both these actions of CCK-8 to a highly significant extent.

The experimental data given above seem fully to support the theory that the use of proglumide may be particularly favourable in the treatment of neoplasia in plastic forms or even causing their regression. This antagonism has been shown by various techniques, both in vivo and in vitro, by the study of the incorporation of tritiated thymidine in the DNA, which incorporation occurs in the S phase of the cell cycle, a phase on which the polypeptide hormones seem to exercise their trophic action.

It has also been shown that proglumide has an effective action even on the endogenous component of these hormones as shown by the increase in the survival time of animals in which colic adenocarcinoma had been implanted and which were treated with proglumide. Pharmaceutical forms including proglumide for use in the treatment of neoplastic affections are of conventional type. They may include pharmaceutically-acceptable inactive ingredients, such as binders, excipients, dispersants, preservatives, humectants and dyes possibly in association with drugs having an antimitotic action.

TABLE 4

Inhibiting action of Proglumide on the rate of growth of normal and tumoral pancreatic cells induced by CCK-8.

| TREATMENT | N° Animals | DOSE | WEIGHT OF THE PANCREAS (mg) | student's t | PANCREATIC DNA (mg) | student's t | WEIGHT OF THE PANCREATIC CARCINOMA (mg) | student's t | TUMORAL DNA | student's t |
|---|---|---|---|---|---|---|---|---|---|---|
| A: Control | 10 | — | 380 ± 29.7 | — | 0.8 ± 0.10 | — | 113 ± 7.66 | — | 0.4 ± 0.05 | — |
| B: CCK-8 | 8(′) | 10 mcg/kg (3 per day) | 600 ± 54.1 | 3.76() | 1.5 ± 0.11 | 4.72(*) | 180 ± 15.2 | 4.17(***) | 0.7 ± 0.13 | 2.79(*) |
| C: Proglumide (PR) | 10 | 250 mg/kg (3 per day) | 330 ± 40.7 | 0.99 | 0.9 ± 0.13 | 0.61 | 100 ± 8.6 | 1.15 | 0.4 ± 0.06 | 0 |
| D: PR + CCK-8 | 10 | 10 mcg/kg CCK-8 + 250 mg/kg PR | 370 ± 38.0 | vsA:0.2 vsB: 3.58() | 1.0 ± 0.09 | vsA:1.56 vsB: 3.56() | 108 ± 8.8 | vsA:0.45 vsB: 4.3(***) | 0.4 ± 0.09 | vsA:0 vsB: 2.33(*) |

(′)2 animals died during the treatment
(*)$p < 0.05$
(**)$p < 0.01$
(***)$p < 0.001$ general and, more particularly, of that which is certainly sustained by endogenous bioactive polypeptides (such as gastrin and CCK), such as gastrointestinal and pancreatic neoplasia.

This treatment may in fact be extremely advantageous in that the rate of proliferation of these tumour cells has been shown to be stimulated and sustained by polypeptides, such as gastrin and cholecystokinin, for which proglumide is a specific antagonist in target cells, that is in gastric cells, colic cells and in the pancreatic acinus. Thus by antagonising these hormones in a selective manner, proglumide may act advantageously in blocking the indiscriminate development of these neo-

We claim:

1. A method of treatment of malignant tumors whose growth is increased by bioactive polypeptides comprising administering an anti-tumor effective amount of proglumide or a pharmaceutically-acceptable salt thereof to a human patient afflicted with said malignant tumors, wherein said malignant tumors are of pancreatic, colic or gastric origin.

2. The method as claimed in claim 1, wherein said bioactive polypeptides are selected from the group consisting of gastrin and cholecytokinin.

* * * * *